US012657220B2

(12) United States Patent
Singh et al.

(10) Patent No.: US 12,657,220 B2
(45) Date of Patent: Jun. 16, 2026

(54) VIRTUAL ASSISTANT FOR GENERATING PRODUCT BASED PROMPT

(71) Applicant: HONEYWELL INTERNATIONAL INC., Charlotte, NC (US)

(72) Inventors: Ankit Singh, Apex, NC (US); Eric Hartye, Oak Ridge, TN (US); Waad Subber, Niskayuna, NY (US); Jason Halpern, Elkins Park, PA (US)

(73) Assignee: HONEYWELL INTERNATIONAL INC., Charlotte, NC (US)

( * ) Notice: Subject to any disclaimer, the term of this patent is extended or adjusted under 35 U.S.C. 154(b) by 88 days.

(21) Appl. No.: 18/642,845

(22) Filed: Apr. 23, 2024

(65) Prior Publication Data

US 2025/0328555 A1 Oct. 23, 2025

(51) Int. Cl.
*G06F 17/30* (2006.01)
*G06F 16/3329* (2025.01)
*G16H 70/40* (2018.01)

(52) U.S. Cl.
CPC ......... *G06F 16/3329* (2019.01); *G16H 70/40* (2018.01)

(58) Field of Classification Search
CPC ........ G06F 16/13; G06F 16/24; G06F 16/156; G06F 3/1297; G06N 3/00; G06N 5/00; G05B 13/00; H03M 7/30; H04N 9/8042; G06T 9/00
See application file for complete search history.

(56) References Cited

U.S. PATENT DOCUMENTS

2023/0124288 A1* 4/2023 Meier-Hellstern ... G06N 3/0455
706/12
2023/0222393 A1* 7/2023 Zahm ...................... G06F 40/35
706/12
2023/0297887 A1* 9/2023 Gurgu ................... G06N 20/00
706/12
2024/0362212 A1* 10/2024 Sun .................. G06F 16/24522
(Continued)

*Primary Examiner* — Hung D Le
(74) *Attorney, Agent, or Firm* — Alston & Bird LLP

(57) ABSTRACT

The present disclosure provides a system for providing virtual assistant for generating customized query for retrieving data from a database. The system comprises a processor and a memory storing program instructions, which, when executed by the processor, causes the processor to provide one or more index of categories of the data, for efficient retrieval of the data from the database based on a customer's query. The processor is also configured to provide one or more few-shot prompts for use by the customer for generating an output in a predetermined format corresponding to the customer's query. The processor is configured to receive a query from the one or more customer, wherein said query is a text and is based on at least one of index of categories and the few-shot prompt. The processor, based on indexes and few-shot prompt processes the query using natural language processing to extract one or more textual content from the query and sends the query to the database for retrieval of the data. The system retrieves the relevant data based on identified textual content, said relevant data is based on semantic similarity between the vector index and displays the retrieved data to the one or more customer based on the predetermined format specified by few-shot prompt.

19 Claims, 10 Drawing Sheets

(56)                References Cited

U.S. PATENT DOCUMENTS

2024/0428138 A1*  12/2024  Manikani ............. G06N 3/0455
2025/0028967 A1*   1/2025  Cai .......................... G06N 3/08
2025/0036874 A1*   1/2025  Nair ..................... G06F 40/295
2025/0036974 A1*   1/2025  Arumugam ............ G06N 20/20
2025/0045316 A1*   2/2025  Lee ..................... G06F 16/3344
2025/0086211 A1*   3/2025  Bolcer ............... G06F 16/3344
2025/0142370 A1*   5/2025  Kasap .................. H04L 41/145
2025/0191337 A1*   6/2025  Willmott ............. G06V 10/761
2025/0200931 A1*   6/2025  Khattak ................ G06V 10/82
2025/0272317 A1*   8/2025  Aggarwal ........... G06F 16/3329

* cited by examiner

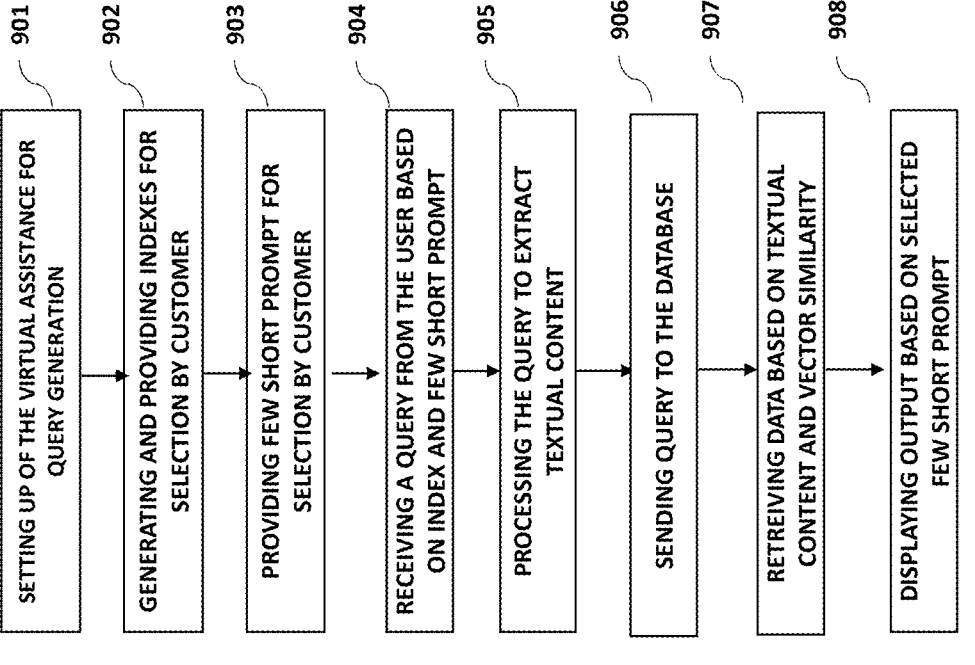

901 SETTING UP OF THE VIRTUAL ASSISTANCE FOR QUERY GENERATION

902 GENERATING AND PROVIDING INDEXES FOR SELECTION BY CUSTOMER

903 PROVIDING FEW SHORT PROMPT FOR SELECTION BY CUSTOMER

904 RECEIVING A QUERY FROM THE USER BASED ON INDEX AND FEW SHORT PROMPT

905 PROCESSING THE QUERY TO EXTRACT TEXTUAL CONTENT

906 SENDING QUERY TO THE DATABASE

907 RETREIVING DATA BASED ON TEXTUAL CONTENT AND VECTOR SIMILARITY

908 DISPLAYING OUTPUT BASED ON SELECTED FEW SHORT PROMPT

Figure 9

1001 — STORING THE DATA IN A DATABASE

1002 — VECTOR EMBEDDINGS BASED ON DATA STORED IN THE DATABASE

1003 — ACCESSING THE INDEXES AND EMBEDDINGS STORED IN THE VECTOR DATABASE

1004 — APPLYING ONE OF MORE FILTERS TO CREATE INDEXES

1005 — CREATING INDEX STRATEGIES FOR USER

1006 — SELECTING AN INDEX STRATEGY BY USER WHILE GENERATING QUERY

VIRTUAL ASSISTANT FOR GENERATING PRODUCT BASED PROMPT

FIELD OF THE INVENTION

The present disclosure generally relates to generating prompts for accessing and generating information. Particularly, the present disclosure provides a system and a method for providing a virtual assistant for generating one or more prompts based on products details stored in a database.

BACKGROUND OF THE INVENTION

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also correspond to implementations of the claimed technology.

In general, companies or entities which manufactures products such as healthcare products, devices/medicines issue annual reports and such annual reports including other information pertaining to such medicines/devices/healthcare products are generally accessible by the customer/end users through different sources such as company website or other common portals which aggregate multiple reports of one or more companies. The information pertaining to products may include its performance statistics, trial results, details of clinical trials, efficacy information etc. A common end user who wish to view such reports, generally is able to download such reports and make conclusions based on such reports.

However, due to varying nature of such reports and nature of information stored in different reports, only limited information is accessible and understood by the user. Though the user may initiate his query based on such stored reports, however, the user may not be able to retrieve relevant information pertaining to his queries due to varying nature of information stored in the database and a simple query based on text is unable to retrieve the relevant information which may be useful for the end user. It is generally known that the data from one or more companies or entities are stored in a database and generally, the database stores the data by generating indexes based on product categories and identifies vector similarities between different data to cluster them in one group. A user's simple textual query is however, unable is retrieve the relevant information, as the query will fetch information irrespective of indexes and vector similarities and may provide users with informations which may not be accurate. Also, the user may want to retrieve information in a particular format or sequence, which is generally not accessible based on simple retrieving of information from the database. Currently, there is no process or system, which may provide users with relevant information, and further information in desired format which is easy to read and access.

Through applied effort, ingenuity, and innovation, the inventors have solved the above problem(s) by developing the solutions embodied in the present disclosure, the details of which are described further herein.

SUMMARY OF THE INVENTION

In general, embodiments of the present disclosure herein provide a method and a system for providing a virtual assistant for generating one or more prompts based on indexes and few-shot prompts to retrieve one or more information relating to a product stored in a database. Other implementations will be, or will become, apparent to one with skill in the art upon examination of the following figures and detailed description. It is intended that all such additional implementations be included within this description be within the scope of the disclosure and be protected within the scope of the following claims.

In one embodiment, the present disclosure provides a system for providing virtual assistant for generating customized query for retrieving data from a database. The system comprises a processor and a memory storing program instructions, which, when executed by the processor, causes the processor to provide one or more index of categories of the data, for efficient retrieval of the data from the database based on a customer's query. The processor is also configured to provide one or more few-shot prompts for use by the user for generating an output in a predetermined format corresponding to the user's query. The processor is configured to receive a query from the one or more user, wherein said query is a text and is based on at least one of index of categories and the few-shot prompt. The processor, based on indexes and few-shot prompt processes the query using natural language processing to extract one or more textual content from the query and sends the query to the database for retrieval of the data. The system retrieves the relevant data based on identified textual content, said relevant data is based on semantic similarity between the vector index and displays the retrieved data to the one or more users based on the predetermined format specified by few-shot prompt.

In another aspect, the present disclosure provides a method for providing a virtual assistant for generating a customized query for retrieving data from a database, comprising. The method comprises providing one or more index of categories of the data, for efficient retrieval of the data from the database based on a customer's query. Further, one or more few-shot prompts are provided to the user for use for generating an output in a predetermined format corresponding to the customer's query. A query is received from the one or more uses, said query is a text and is based on at least one of index of categories and the few-shot prompt. The method further comprises processing the query using natural language processing to extract one or more textual content from the query and sending the query to the database for retrieval of the data. Further, the relevant data is retrieved based on identified textual content, said relevant data is based on semantic similarity between the vector index. Further, the retrieved data is displayed on the user interface of the one or more users based on the predetermined format specified by few-shot prompt.

In yet another embodiment, the present disclosure provides non-transitory computer-readable storage medium storing program instructions for providing a virtual assistant for generating a customized query for retrieving data from a database, the instructions, when executed, perform the steps of providing one or more index of categories of the data, for efficient retrieval of the data from the database based on a user's query. Further, one or more few-shot prompts are provided to the user for generating an output in a predetermined format corresponding to the user's query. A query is received from the one or more user, said query is a text and is based on at least one of index of categories and the few-shot prompt. Further, the query is processed using natural language to extract one or more textual content from the query and sending the query to the database for retrieval of the data. Further, the relevant data is retrieved based on identified textual content, said relevant data is based on semantic similarity between the vector index. Further, the retrieved data is displayed on the user interface of one or more users based on the predetermined format specified by few-shot prompt.

The above summary is provided merely for the purpose of summarizing some exemplary embodiments to provide a basic understanding of some aspects of the present disclosure. Accordingly, it will be appreciated that the above-described embodiments are merely examples and should not be construed to narrow the scope or spirit of the present disclosure in any way. It will be appreciated that the scope of the present disclosure encompasses many potential embodiments in addition to those here summarized, some of which will be further described below. Other features, aspects, and advantages of the subject will become apparent from the description, the drawings, and the claims.

BRIEF DESCRIPTION OF THE DRAWINGS

Figure 1:
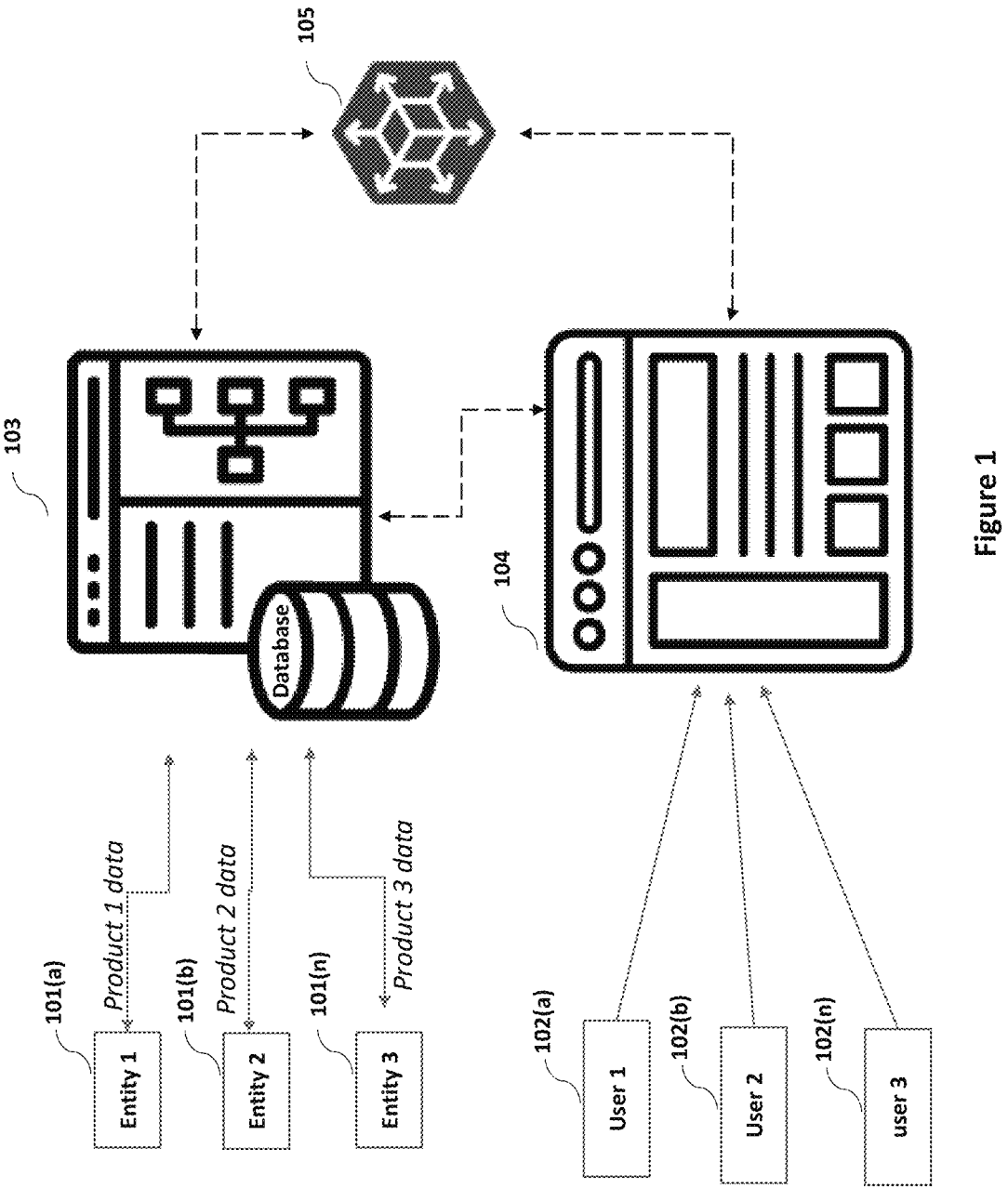

Having thus described the embodiments of the disclosure in general terms, reference now will be made to the accompanying drawings, which are not necessarily drawn to scale, and wherein:

FIG. 1 illustrates an architecture of a system for providing virtual assistance for generating customized query for retrievable of information, in accordance with an embodiment of the present invention.

Figure 2:
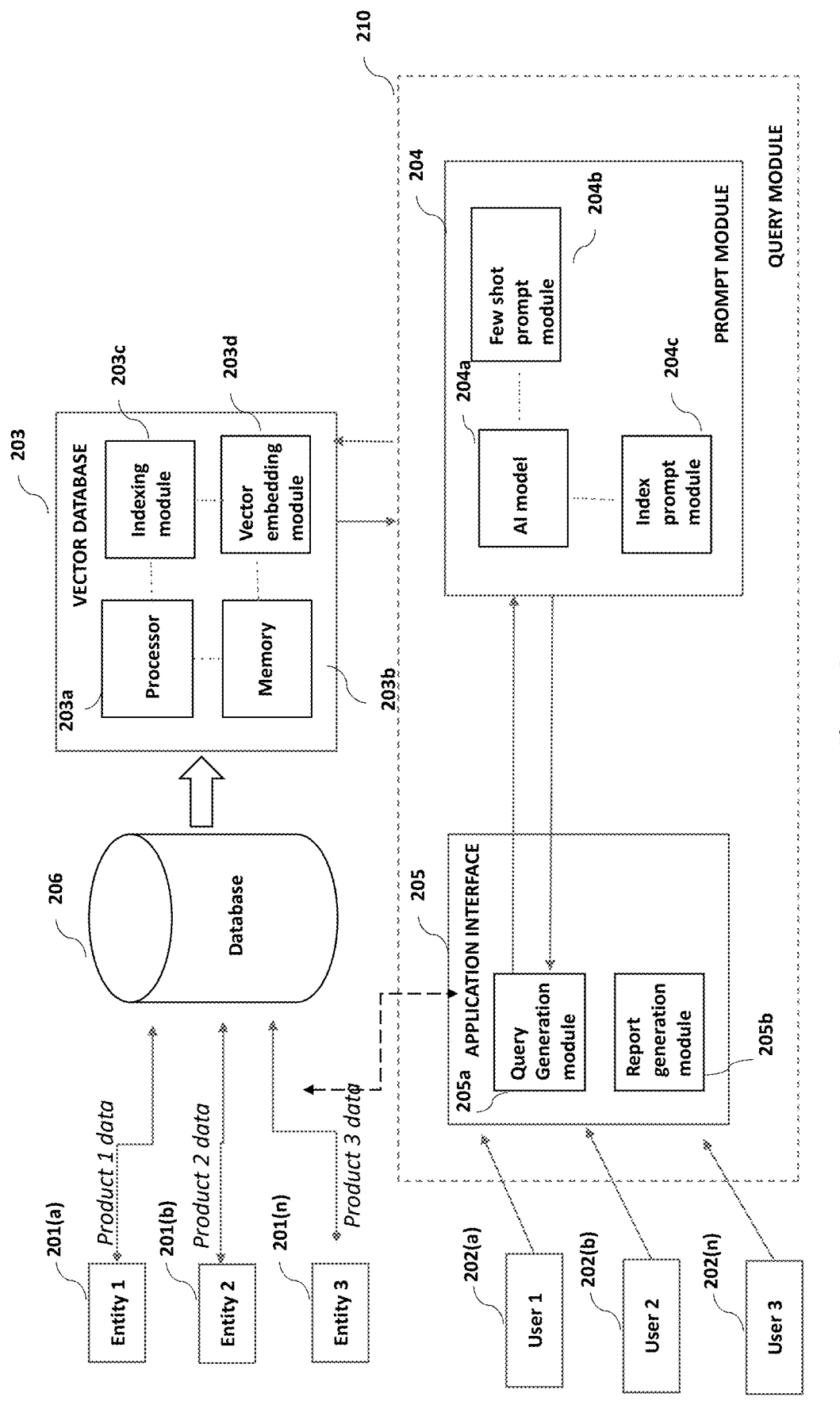

FIG. 2 illustrates a block diagram of module-based operation of the system, in accordance with an embodiment of the present invention.

Figure 3:
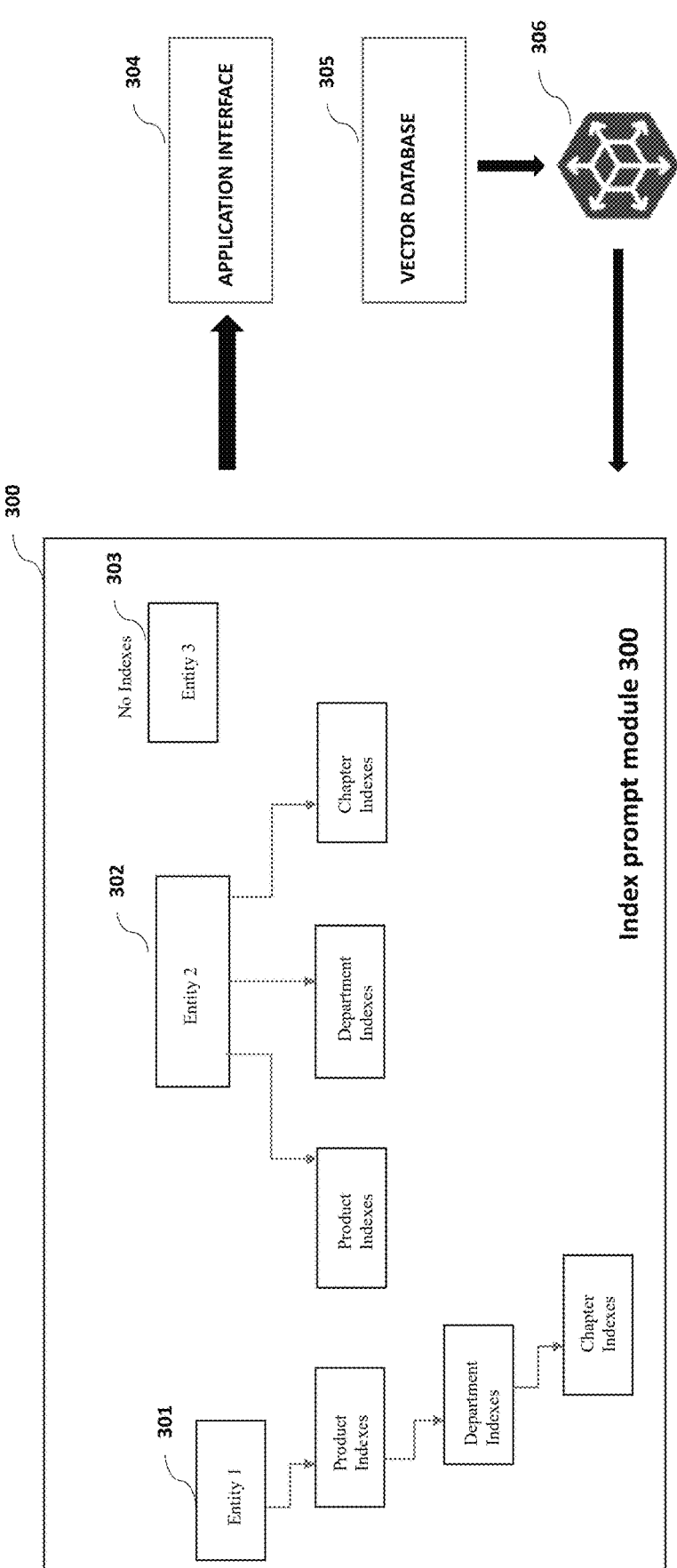

FIG. 3 illustrates different types of data indexing in accordance with an embodiment of the present invention.

Figure 4:
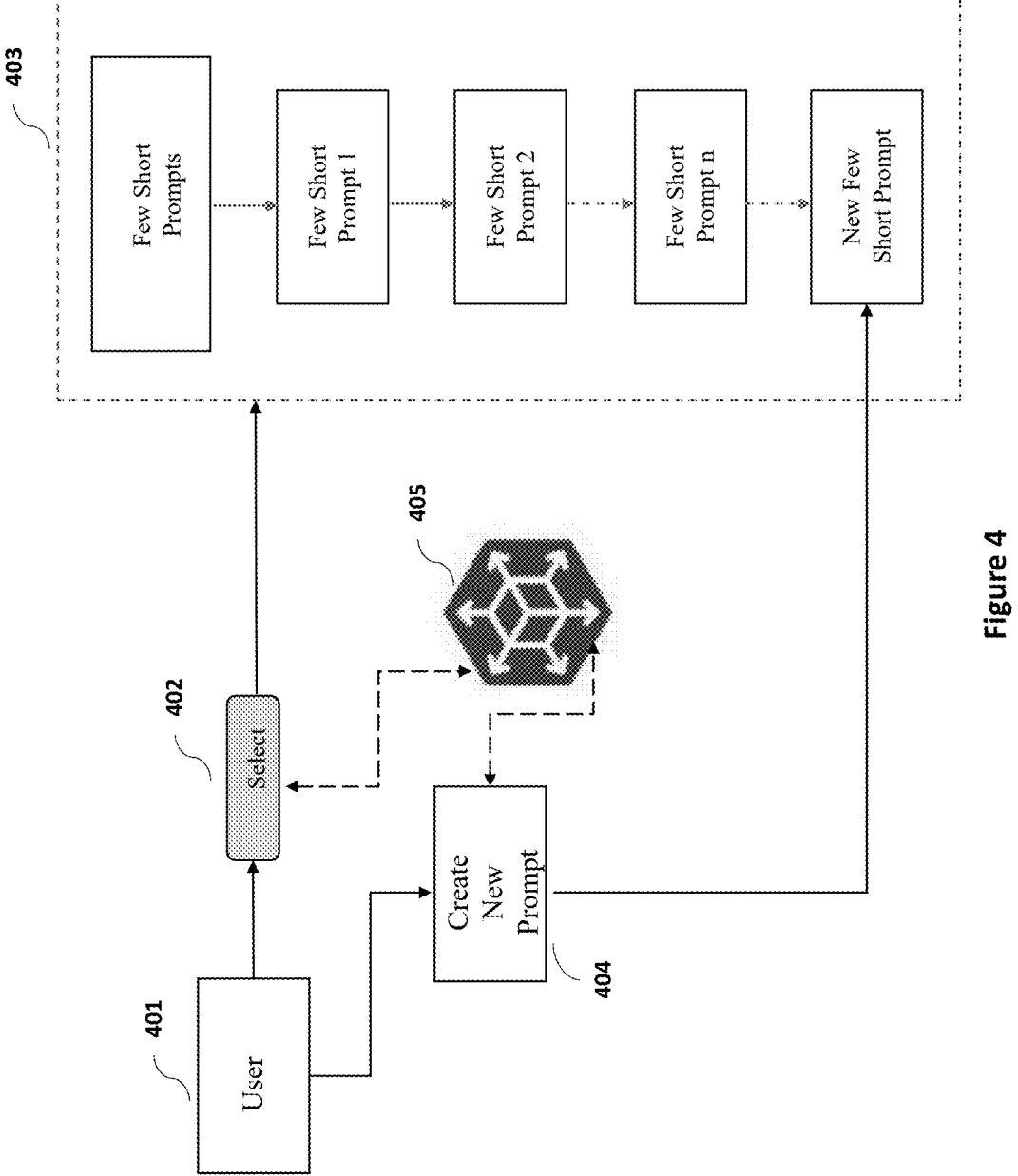

FIG. 4 illustrates different types of few-shot prompts and its selection, in accordance with an embodiment of the present invention.

Figure 5:
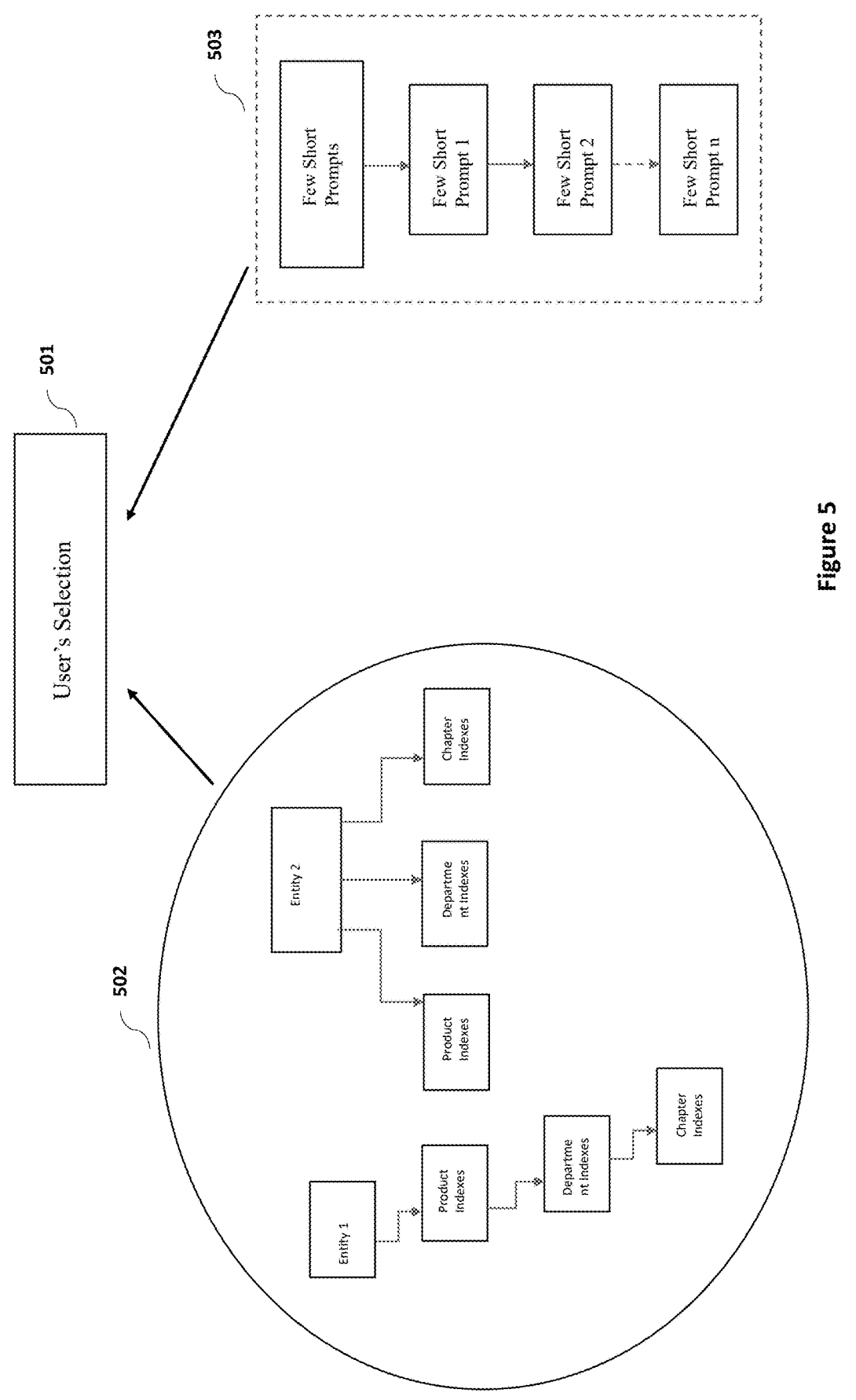

FIG. 5 illustrates selection of indexes and few-shot prompt by customer for generating customized query, in accordance with an embodiment of the present invention.

Figure 6:
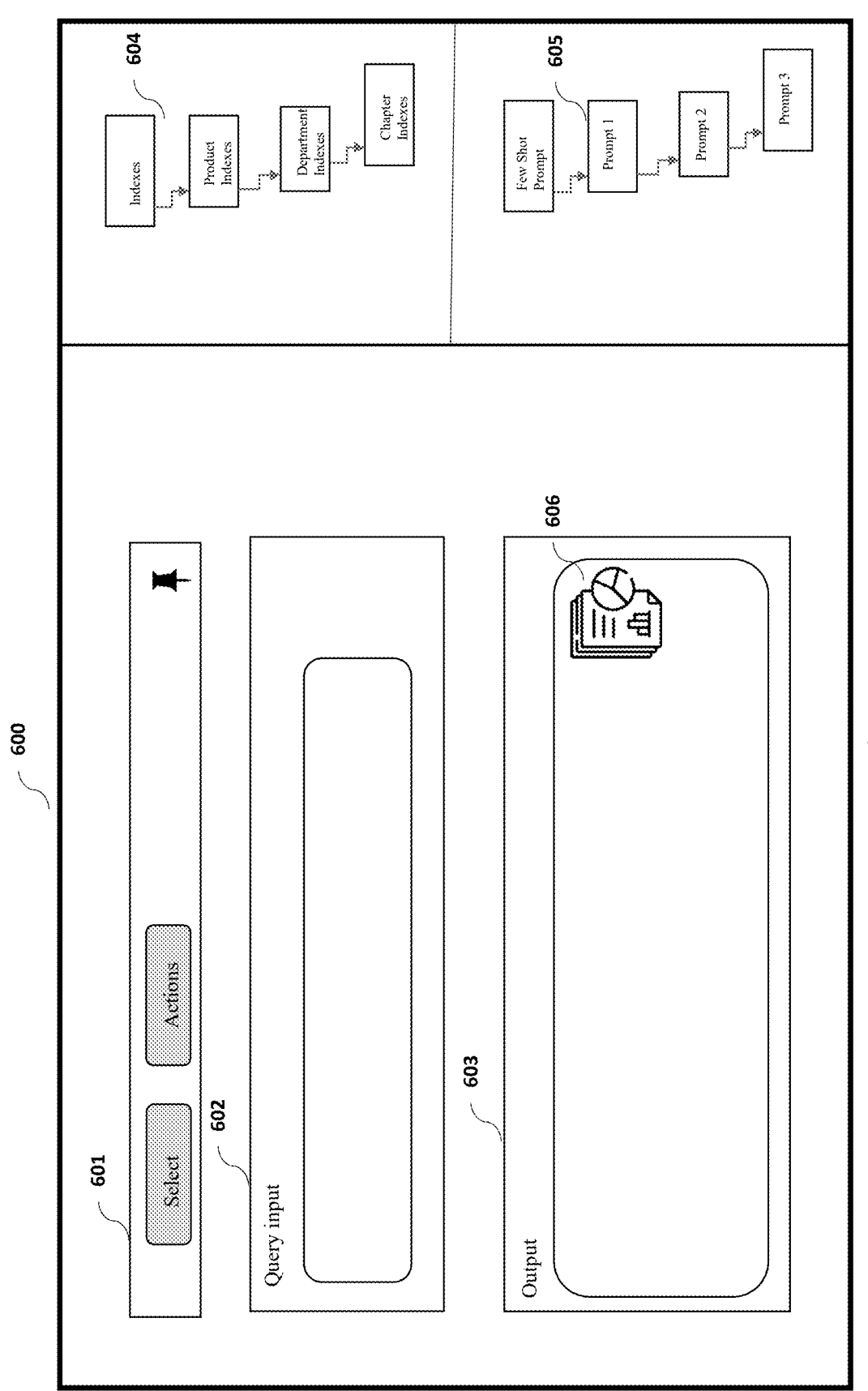

FIG. 6 illustrates an exemplary user interface for generating customized query based on selection of indexes and few-shot prompt, in accordance with an embodiment of the present invention.

Figure 7:
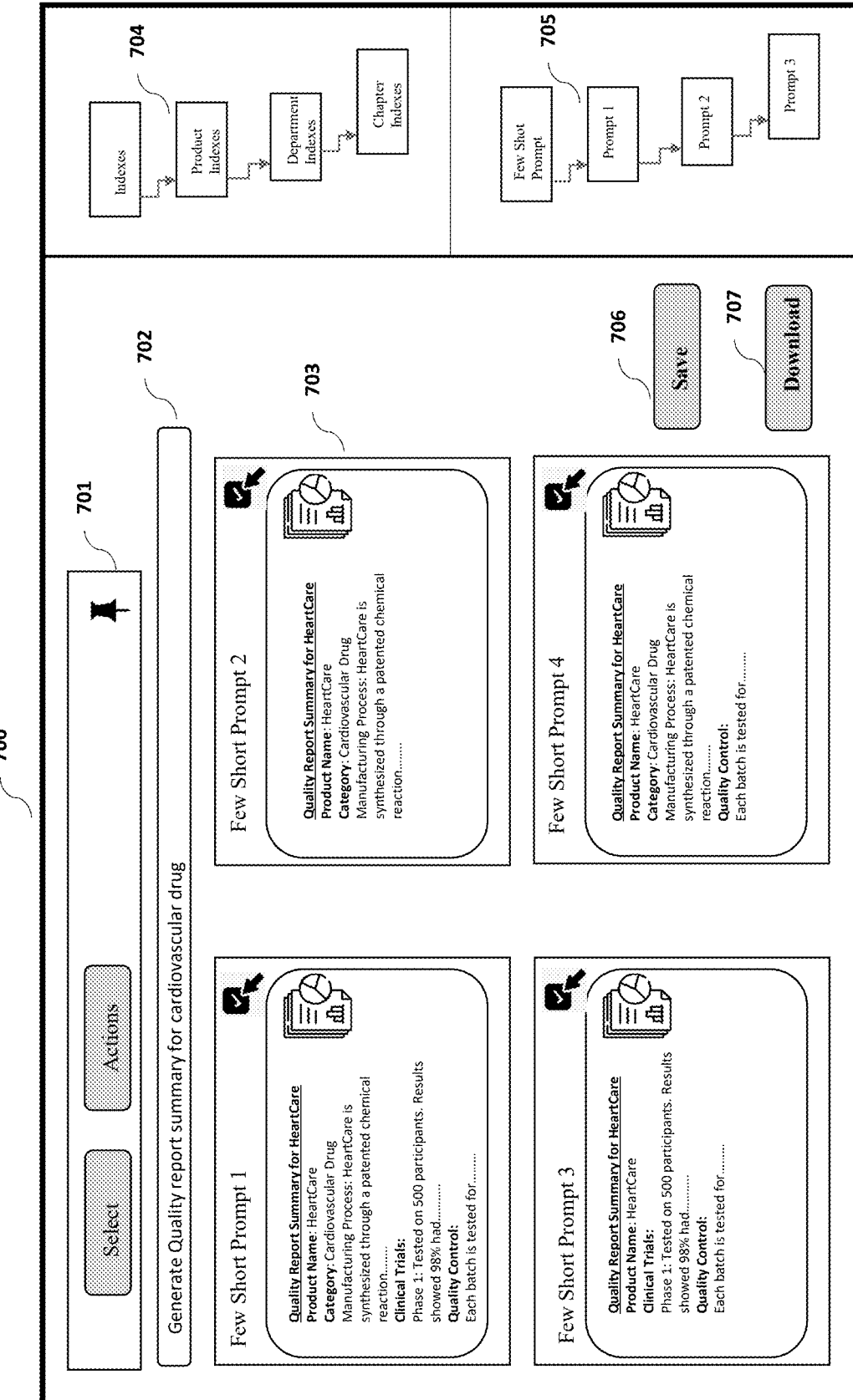

FIG. 7 illustrates an exemplary user interface illustrating the output based on customer's query, in accordance with an embodiment of the present invention.

Figure 8:
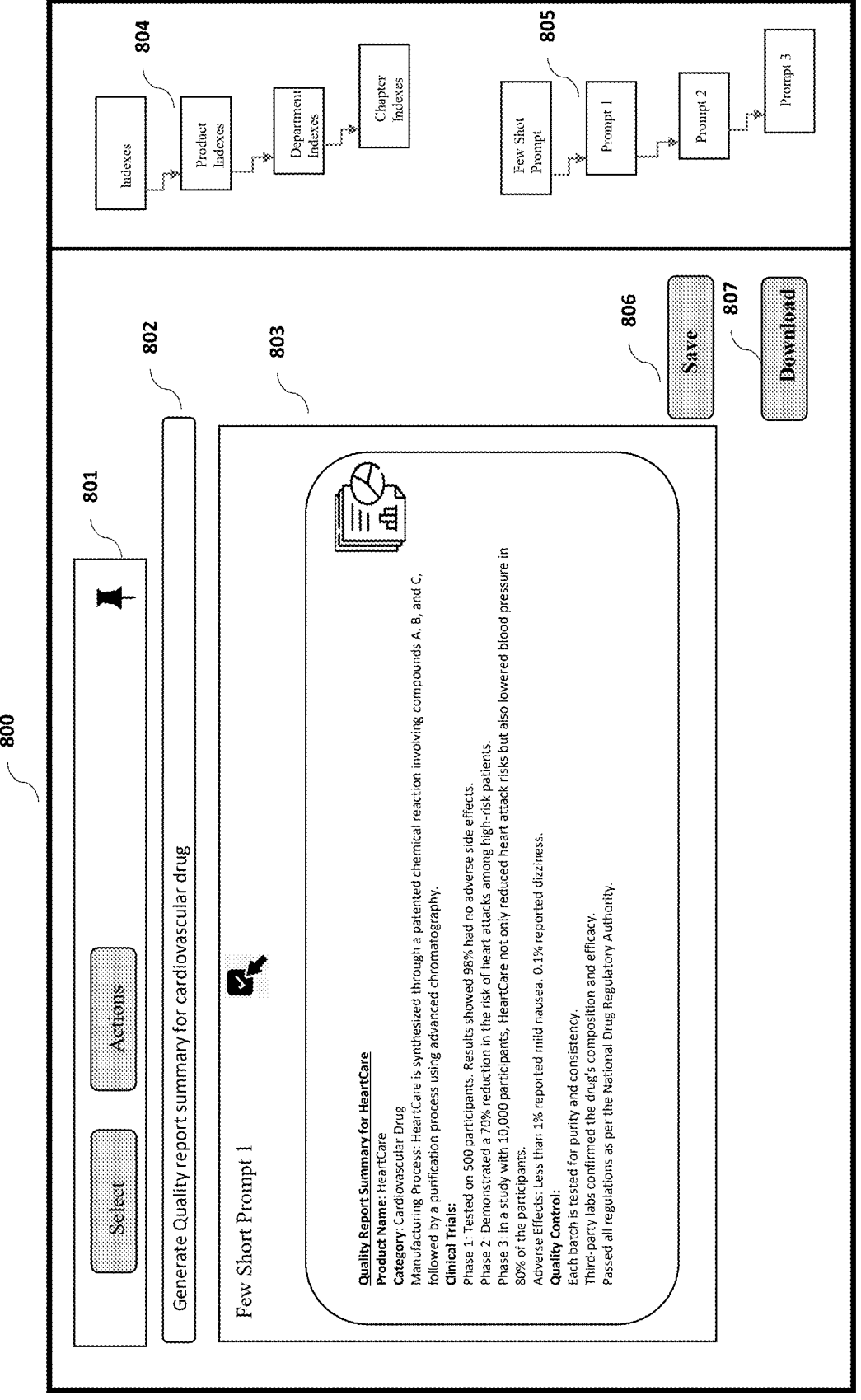

FIG. 8 illustrates an exemplary user interface illustrating the output based on selected few-shot prompt, in accordance with an embodiment of the present invention.

Figure 10:
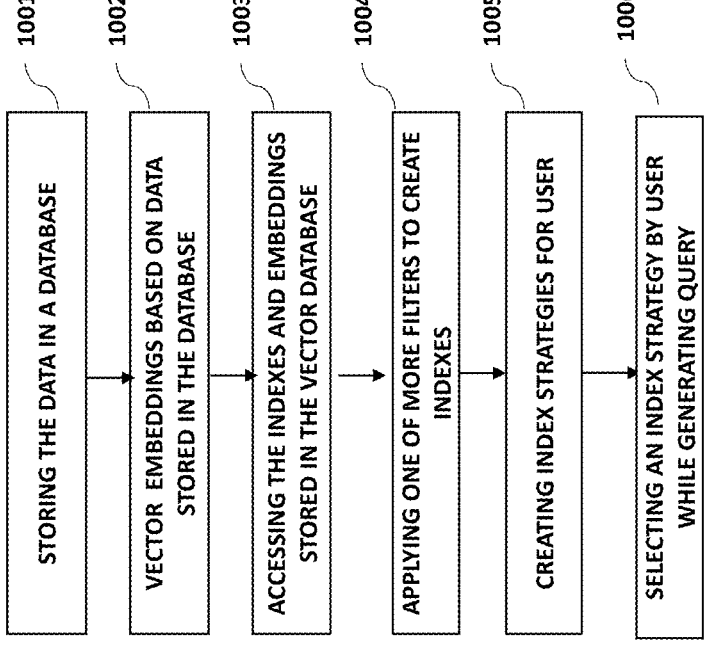

FIG. 9 illustrates the method steps for providing virtual assistance for generating customized query for retrievable of information, in accordance with an embodiment of the present invention; and FIG. 10 illustrates the method steps for generating indexes based on data stored in the vector database, in accordance with an embodiment of the present invention.

DETAILED DESCRIPTION OF THE INVENTION

The detailed description set forth below in connection with the appended drawings is intended as a description of various embodiments of the present invention and is not intended to represent the only embodiments in which the present invention may be practiced. Each embodiment described in this invention is provided merely as an example or illustration of the present invention, and should not necessarily be construed as preferred or advantageous over other embodiments. The detailed description includes specific details for the purpose of providing a thorough understanding of the present invention. However, it will be apparent to those skilled in the art that the present invention may be practiced without these specific details.

Some embodiments of the present disclosure now will be described more fully hereinafter with reference to the accompanying drawings, in which some, but not all, embodiments of the disclosure are shown. Indeed, embodiments of the disclosure may be embodied in many different forms and should not be construed as limited to the embodiments set forth herein, rather, these embodiments are provided so that this disclosure will satisfy applicable legal requirements. Like numbers refer to like elements throughout.

As used herein, the term "comprising" means including but not limited to and should be interpreted in the manner it is typically used in the patent context. Use of broader terms such as comprises, includes, and having should be understood to provide support for narrower terms such as consisting of, consisting essentially of, and comprised substantially of.

The phrases "in one embodiment," "in another embodiment", "according to one embodiment," "in some embodiments," and the like generally mean that the particular feature, structure, or characteristic following the phrase may be included in at least one embodiment of the present disclosure, and may be included in more than one embodiment of the present disclosure (importantly, such phrases do not necessarily refer to the same embodiment).

The word "example" or "exemplary" is used herein to mean "serving as an example, instance, or illustration." Any implementation described herein as "exemplary" is not necessarily to be construed as preferred or advantageous over other implementations The present disclosure relates to a system and method for providing a virtual assistant for generating a customized query for retrieving data from a database. In general, the entities manufacture one or more goods which may include medical devices, healthcare related products and the reports associated with said products including clinical trials, efficacy data, trial data and other related details are stored in the database. While an end user who is desirous of accessing such information relating to one or more such products, can run a general search query and execution of such query may return results to the end user. However, such results which are provided to the end user may not accurate as the information is stored in the database with indexes and the user's query may be a simple textual based query. In many instances, where one or more products exists in different category, a simple query may yield irrelevant results to the end user. There is a need for a system and method, which would enable the user to search for relevant information using indexes which may yield relevant results based on similarity vector indexing and also, based on few shot prompts which provides customized reports to the end user, thereby making query generation process and results retrievable become more relevant and useful.

FIG. 1 illustrates an exemplary network architecture of the system for providing a virtual assistant for generating a customized query for retrieving data from a database, in accordance with an embodiment of the present invention. One or more entities 101*a* . . . 101*n* are involved in manufacturing and distribution of one or products and said products may include healthcare related products including medical devices, medicines, therapeutic compositions. The entities 101a . . . 101n are configured to access the database 103 through a network and store one or more information relating to said products in the memory of the database. In an embodiment, the database is a cloud-based database. In another embodiment, the database may be localized database. The database 103 is configured to save the data obtained from one or more entities and save the data in a structured manner.

In an embodiment, the database 103 is configured to save the data related to one or more products pertaining to plurality of entities based on vector indexes and embeddings. An embedding is a representation of words, sentences, images etc., summarized as an array of numericals, i.e., vectors and these embeddings captures semantic information about one or more terms or phrase. In an embodiment, the database 103 processes the data by establishing relationship between two or more products and create indexes based on relationship. Further, semantic similarity or relatedness of products are established using natural language processing and one or more relationships between various products, entities are created based on similarity scores. The database 103 enables for an effective retrieval system based on vector similarities.

The system also depicts one or more users 102a . . . 102n who are desirous of accessing data stored in the database 103 to obtain relevant results based on their search query. The users 102a . . . 102n access the database 103 through an user interface 104. In an embodiment, the user interface 104 is configured to receive the user's query, process the query to identify the semantics of the terms and phrases. In a further embodiment, the user interface 104 is further configured to provide the user one or more indexes to choose the category for which the search query is most relevant and also, provide the customer one or more few-shot prompts to obtain the customized output based on search query.

The system also provides a machine learning model 105 which steers the query generation process by learning about the patterns and selection by one or more customers based on their access. In an embodiment, few-shot prompting is used as a technique to enable in-context learning where the demonstrations may be provided in the prompt to steer the model to better performance. A more detailed embodiments of system according to the present disclosure is explained in FIG. 2.

In an embodiment, an entity may be a business entity, an organization, a data warehouse, or any separate, standalone entities. Further, each user is associated with a user device and the user devices may refer to, for example, one or more computers, computing entities, desktop computers, mobile phones, tablets, phablets, notebooks, laptops, distributed systems, servers, or the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein.

FIG. 2 illustrates an exemplary module-based architecture for providing a virtual assistant for generating a customized query for retrieving data from a database. As explained above with respect to FIG. 1 above, one or more entities 201a . . . 201n are involved in manufacturing and distribution of one or products and the products may include healthcare related products including medical devices, medicines, therapeutic compositions. The entities 201a . . . 201n are configured to access the database 206 via a network and store one or more information relating to said products in the memory of the database. In an embodiment, the database is a cloud-based database.

In another embodiment, the database may be localized databased. The database 206 is configured to save the data obtained from one or more entities and save the data in a structured manner. In an embodiment, a vector database 203 is provided which is coupled to the database 206. The vector database 203 is configured to save the data related to one or more products pertaining to plurality of entities based on vector indexes and embeddings. The vector database 203 processes the data by establishing relationship between two or more products and create indexes based on relationship. Further, semantic similarity or relatedness of products are established using natural language processing and one or more relationships between various products, entities are created based on similarity scores.

In an embodiment, the vector database 203 can be discrete to the database 206. In another embodiment, the vector database 203 and the database 206 are integrated to save the data received from the entities 201a . . . 201n in vector-based structure for easy access and retrieval. Vector databases are storage systems specialized in storing large amounts of vectors, and providing efficient search over the vectors. Some popular open source vector databases include Milvus, Weaviate, and Qdrant. These databases implement various strategies for indexing input vectors and efficient vector search. They also take care of other properties for using vector search in production, e.g., scalability, auto-tuning.

One or more users 202a . . . 202n who are desirous of accessing data stored in the database 203 to obtain relevant results based on their search query. The user 202a . . . 202n access the database 203 through a query module 210. The query module 210 according to the present disclosure comprises an application interface 205 and a prompt module 204. The application interface 205 further comprises a query generation module 205a and a report generation module 205b. In a further embodiment, the prompt module 204 comprises an AI model 204a, few shot prompt module 204b and Index prompt module 204c. The application interface 205 and the prompt module 204 are coupled to each other for processing of the user's query and provides indexing prompt and few-shot prompt to the user, which is further explained below.

The query generation module 205a is configured to receive the user's query. The user's query in an embodiment may be related to one or more products saved in the database 203, 206. The user's query may be a simple text-based query which is processed by the natural language processing technique to identify the key terms and relationships between one or more words included in the search query. In an embodiment, an AI Model 204a is provided which is configured to process the user's query to generate vector index and vector embeddings.

Further, the user's query though the application interface may be based on index prompt and few-shot prompt. The index prompt module 204c is configured to provide the customer one or more index-based searching capabilities. Further, the few shot prompt module 204b is configured to provide one or more few shot prompts to the customer for selection, based on preferred format of the output.

The user's query generated according to the indexing and the few shot prompt is forwarded to the database for retrieving the relevant results based on semantic vector similarity between the query and information stored in the database 203. One or more search results are retrieved based on semantic similarity or vector similarity between the user's query and data stored in the vector database. In an embodiment, the vector embeddings of the search query are compared with the vector embeddings of the data stored in the database and based on similarly score, relevant data is retrieved. In an example, a similarity score may be assigned and the data is retrieved based on matching vector embeddings if the similarity score is above a threshold level. The system is further configured to change the threshold on the similar score if the retrieved results are not matching the quality score.

In another embodiment, the database may be configured to provide results based on standard queries. In an example, one or more predetermined search results may be configured to be generated based on specific prompt. Providing predetermined results based on standard prompts saves the resources in comparing semantic similarity, thereby making the search system efficient.

The retrieved result in presented to the report generation module 205b. In one embodiment, the result is displayed according to one few shot prompt chosen by the customer. In another embodiment, the result may be displayed according to plurality of few shot prompt and the user may select one or more of the displayed results for review and access. Further, in another embodiment, the report generation module further provides for downloading of reports in a printable format. FIG. 3 and FIG. 4 further discusses the indexing strategy and few-shot prompt for the customer enabling effective retrievable of the stored data.

In an embodiment, one or more modules of the system may be implemented using one or more processor(s) or said modules may be hardware, computer software, or any combination thereof.

In an embodiment, the functional units have been labeled as modules, in order to more particularly emphasize their implementation independence. For example, a module may be implemented as a hardware or a software by various types of processors. A module of executable code may, for instance, comprise one or more physical or logical blocks of computer instructions, which may, for instance, be organized as an object, procedure, or function. Nevertheless, the executables of a module need not be physically located together, but may comprise disparate instructions stored in different locations which, when joined logically together, comprise the module and achieve the stated purpose for the module.

FIG. 3 illustrates a strategy for generating and providing indexes for the user for generating queries. An Index Prompt Module 300 is provided which is configured to generate indexes for the customer and displays the same on the application interface 304 for the user while generating the queries. In an embodiment, the index prompt module 300 is coupled to the Vector database 305 and the index prompt module 300 is configured to generate one or more type of indexes based on the entities data stored in the database. Each entity's data includes multiple products based on different categories and hence, the indexing is created based on each entity data and its products. In an embodiment, each entity has a tenant index and further indexes such as product indexes, Department indexes, Chapter Indexes may be created based on entities requirements. The tenant index represents attributes representing an entity. The product index represents attributes representing one or more characteristics of the product. The Department index represents attributes of the relevant department pertaining to one or more products. The Chapter index may represent attributes relating to operating status such as manufacturing, trial phase, research phase etc.

One or more various types of indexing strategy according to an embodiment of the present invention is provided. In one implementation, the index prompt module 300 may generate hierarchical indexing 301 which represents entity, product index, Department Index and Chapter Index in a hierarchical manner. In other implementation, the index prompt module 300 is configured to generate flat indexing 302 wherein the product index, Department Index and Chapter Index are directly linked to the entity. In another embodiment, no indexing 303 may be provided and all the data pertaining to the entity may be accessed without indexing selection. One or more entities may generally choose one or more type of indexing of their product data which is stored in the database.

The Index Prompt module 300 is coupled to the vector database 305 and is configured to generate one or more indexing based on vector database and provide the indexing for the user's selection for generating a query. In an embodiment, the index Prompt Module 300 is coupled to AI model 306 and is configured to access the indexes stored in the vector database 305 and accordingly, creates one or more indexing strategies for the user's selection while generating a search query. In an implementation, when the user is inputting a search query, the Index prompt module 300 provides prompt to the user and provide one or more indexing strategies for the user's selection, so that the retrievable of the search results may be more accurate. In one embodiment, the user may refrain from selecting an indexing strategy and continue to input the search without any indexing criteria.

Provided below is an example of how to apply filters while retrieving embeddings from a vector store. Firstly, create a vector store with the desired documents and embeddings. In an example, a specific vector store can be used for implementation like ElasticsearchStore or TimescaleVector, or custom vector store can be created. Once the vector store is created, the processor uses the similarity_search method to retrieve embeddings based on a query. This method allows to pass additional parameters, including filters.

To apply filters, the processor can pass a filter parameter to the similarity_search method. The filter parameter should be a dictionary that specifies the filtering conditions based on the metadata of the documents. For example, if a "department" metadata field is provided and you want to retrieve embeddings only for documents with the department as "manufacturing", the following filter can be used:

filter={"metadata": {"department": "manufacturing"}}

In another implementation, the processor may also apply multiple filters by using nested dictionaries or lists. For example, if embeddings for documents with the product as "Tylenol, "department as "Manufacturing" and chapter type as "manufacturing" is required to be retrieved, the following filter can be used:

```
filter={
    "metadata": {
        "product": "Tylenol",
        "department": "manufacturing",
        "chapter type": "manufacturing"
    }
}
```

Pass the filter parameter to the similarity_search method along with the query. The method will return the embeddings that match the query and the specified filters.

Provided below is an example code snippet that demonstrates the application of filters while retrieving embeddings from a vector store:

from langchain.vectorstores import ElasticsearchStore

```
from langchain.embeddings import OpenAIEmbeddings
# Create the vector store
embeddings=OpenAIEmbeddings( )
vectorstore=ElasticsearchStore.from_documents(docs,
    embeddings)
# Define the filter
filter={"metadata": {"genre": "science fiction"}}
# Retrieve embeddings with filters
embeddings=vectorstore.similarity_search(query,
    filter=filter)
```

In this example, the documents variable represents the documents in the vector store, and the query variable represents the query for similarity search. The filter variable specifies the filter conditions based on the metadata field "genre". The embeddings variable will contain the retrieved embeddings that match the query and the specified filters. It is pertinent to adjust the code according to the specific vector store implementation and the structure of your documents' metadata.

FIG. 4 illustrates strategy for generating and providing few-shot prompts for the user's selection. The few shot prompt module 403 is configured to generate one or more few-shot prompt for outputting the search results based on user's query. The AI model 405 is coupled to the few shot prompt module 403 and is configured to generate plurality of few-shot prompts 403(1) . . . 403(*n*) which may be selected by the user while generating a query. In another embodiment, the user may generate a new few shot prompt based on his own requirements/preference and the same is provided to the create new prompt module 404. In a further embodiment, the new shot prompt as created by the user is used to train the AI model 405 and add the new created few-shot prompt to the repositories.

In an implementation, when the user begins inputting the query, the application interface provides for user's selection one or more few-shot prompts for generating output results in a preferred format. The user may select one or more few-shot prompts from the application interface and the output results will be created based on the selected few-shot prompt.

Few examples of few-shot prompt based output is illustrated below:

Example 1

Quality Report Summary for HeartCare
Product Name: HeartCare
Category: Cardiovascular Drug
Manufacturing Process: HeartCare is synthesized through a patented chemical reaction involving compounds A, B, and C, followed by a purification process using advanced chromatography.
Clinical Trials:
Phase 1: Tested on 500 participants. Results showed 98% had no adverse side effects.
Phase 2: Demonstrated a 70% reduction in the risk of heart attacks among high-risk patients.
Phase 3: In a study with 10,000 participants, HeartCare not only reduced heart attack risks but also lowered blood pressure in 80% of the participants.
Adverse Effects: Less than 1% reported mild nausea. 0.1% reported dizziness.
Quality Control:
Each batch is tested for purity and consistency.
Third-party labs confirmed the drug's composition and efficacy.

Passed all regulations as per the National Drug Regulatory Authority.

Example 2

Quality Report Summary for BrainBoost
Product Name: BrainBoost
Category: Nootropic Drug
Manufacturing Process: BrainBoost capsules are derived from natural extracts of herbs X, Y, and Z. The extraction process retains essential phytonutrients beneficial for cognitive functions.
Clinical Trials:
Phase 1:400 participants showed enhanced short-term memory and focus.
Phase 2: On prolonged use, 65% of the participants reported improved cognitive functions and alertness.
Phase 3: In a diverse group of 7,000 participants, BrainBoost not only enhanced cognitive functions but also showed potential in delaying the onset of Alzheimer's in predisposed individuals.
Adverse Effects: 1.5% reported difficulty in sleeping if taken late in the day. 0.5% reported heightened sensitivity to light.
Quality Control:
Ensured that natural extracts retain their potency through the extraction process.
Each batch undergoes rigorous testing for heavy metals and toxins.
Certified organic and non-GMO.
As evident from the above summaries, the quality report of each drug is tailored to its unique characteristics, manufacturing processes, trial results, and potential side effects. They cater to their specific target groups, uses, and concerns. While "HeartCare" is more focused on cardiovascular benefits and related trials, "BrainBoost" emphasizes cognitive enhancements and its natural origin.

In an example, the user can define such templates using reports from previous years or an automated workflow can extract summaries from various product types from years in the past and use those as examples for few shot learnings. Similar to the executive summary use case, the database may be configured to define standard answers for some most commonly asked questions by the regulatory authorities like FDA, for example for a particular drug they may focus on manufacturing process but on some other drug they may focus on chemical compositions/R&D testing.

The system provides a machine learning model which steers the query generation process by learning about the patterns and selection by one or more user based on their access. few-shot prompting is used as a technique to enable in-context learning where the demonstrations may be provided in the prompt to steer the model to better performance.

FIG. 5 illustrates selection of indexes 502 and few-shot prompts 503 by user for generating customized query, in accordance with an embodiment of the present invention. As depicted, the user 501 while inputting a search query to retrieve results relating to any products and related details for any entity or group of entity, the user is configured to select at least one of indexes 502 and few-shot prompts 503 and the selection of indexes and few-shot prompts enable efficient search results based on user's desired format. In an exemplary embodiment, the user may choose not to select indexes or few-shot prompts while inputting a query.

FIG. 6 illustrates an exemplary user interface 600 for generating customized query based on selection of indexes and few-shot prompt, in accordance with an embodiment of the present invention. As depicted in an exemplary user interface 600, one or more field are provided for use by the user. A portion 602 is provided wherein the user may input his or her queries and said query may be textual comprising combination of one or more words. The query generating module is configured to process the query and generate vector embedding based on semantic analysis of the query phrase. The user interface also provides portion 604 which depicts indexes to be selected by the user. In an exemplary embodiment, the user may utilize "Select" icon to select one or more indexes from the plurality of indexes provided on the user interface. In another embodiment, the user may deny using any indexes for the purpose of initiating the search based on the inputted query.

Further, the user interface also provides a portion 605 which depicts few-shot prompts for selection by the user. The user, based on his preference, may select one or more prompts which is inputted as a pre-condition for generating the output results. In an embodiment, the user may deny using any few-shot prompt and the system may provide the search results according to a predetermined or default format.

In a further embodiment, the user interface may provide an option 606 for downloading the report summarizing the search results. To enable the user to easy download the report, an icon may be provided in the output portion of the user interface and the user may simply access the icon to download and save the reports in the memory.

FIG. 7 illustrates an exemplary user interface 700 illustrating the output based on customer's query, in accordance with an embodiment of the present invention. As depicted in an exemplary user interface 700, one or more field are provided for use by the user. A portion 702 is provided wherein the user may input his or her queries and said query may be textual comprising combination of one or more words. The query generating module is configured to process the query and generate vector embedding based on semantic analysis of the query phrase. The user interface also provides a portion 704 which depicts indexes to be selected by the user. In an exemplary embodiment, the user may utilize "Select" icon to select one or more indexes from the plurality of indexes provided on the user interface. In another embodiment, the user may deny using any indexes for the purpose of initiating the search based on the inputted query.

Further, the user interface also provides a portion 705 which depicts few-shot prompts for selection by the user. The user, based on his preference, may select one or more prompts which is inputted as a pre-condition for generating the output results. In an embodiment, the user may deny using any few-shot prompt and the system may provide the search results according to a predetermined or default format.

As depicted in portion 703 of the user interface, one or more output relating to search query is provided according to the user's selection of few-shot prompts. In an exemplary embodiment, the user may select one or many outputs based on selection icon and generate a report using the "download" icon. Also, the query results are saved in the memory using the "save" icon.

FIG. 8 illustrates an exemplary user interface 800 illustrating the selection of search results, in accordance with an embodiment of the present invention. In an exemplary embodiment, based on selection of one search result, the other search results may be discarded and the portion 803 of the user interface 800 displays the selected search results for display and download using the "download" icon.

FIG. 9 illustrates the method steps for providing virtual assistance for generating customized query for retrievable of information, in accordance with an embodiment of the present invention.

In Step 901, a virtual assistance for query generation is set up for the user. The user is provided with an application interface which provides at least one portion for inputting the query. The query may be a textual query including combinations of one or more words, phrase. In the initial set up, the system is configured to generate indexes and few-shot prompts for selection by the user while inputting the query.

In Step 902, the system provides for generating and providing indexes for selection by the user. In the system, the database 206 is configured to save the data obtained from one or more entities and save the data in a structured manner. In an embodiment, a vector database 203 is provided which is coupled to the database 206. The vector database 203 is configured to save the data related to one or more products pertaining to plurality of entities based on vector indexes and embeddings. The vector database 203 processes the data by establishing relationship between two or more products and create indexes based on relationship. Further, semantic similarity or relatedness of products are established using natural language processing and one or more relationships between various products, entities are created based on similarity scores. In step 902, the Index Prompt Module 204c is configured to generate indexes for the customer and displays the same on the application interface for the user while generating a query. In generating the indexes, the index prompt module is coupled to the Vector database 203 and is configured to generate one or more type of indexes based on the entity's data stored in the database. Each of the entity data includes multiple products based on different categories and hence, the indexing is created based on each entities data and its products.

In generating the indexes, the index Prompt Module 204c is coupled to AI model 204a and is configured to access the indexing stored in the vector database 203 and accordingly, creates one or more indexing strategies for the user's selection. In one embodiment, the index prompt module 204c applies filters while retrieving embeddings from a vector store and use the similarity search method to retrieve embeddings based on a query. This method allows to pass additional parameters, including filters. For example, the indexing generated by Index prompt module may include hierarchical indexing which includes product indexes, Department indexes, Chapter Indexes. Based on entities data stored in the database and its vector indexing, the index prompt module is configured to generate a different type of indexing such as hierarchical indexing, flat indexing.

In Step 902, after generating indexes based on vector database, the index prompt module is further configured to provides prompt to the user for selection of one or more index strategy when the user is inputting a search query. The user may refrain from selecting an indexing strategy and continue to input the search without any indexing criteria. The user interface provides a portion which depicts indexes to be selected by the user. In an exemplary embodiment, the user may utilize "Select" icon to select one or more indexes from the plurality of indexes provided on the user interface. In another embodiment, the user may deny using any indexes for the purpose of initiating the search based on the inputted query.

In Step 903, the system provides for generating and providing few-shot prompt for selection by the user. In generating the few-shot prompt, the few shot prompt module 204*b* is configured to generate one or more few-shot prompt for outputting the search results based on user's query. The AI model 204*a* is coupled to the few shot prompt module 204*b* and is configured to generate plurality of few-shot prompts which may be selected by the user while generating a query. In another embodiment, the user may generate a new few shot prompt based on his own requirements/preference and the same is provided to the create new prompt module.

In a further embodiment, the new shot prompt as created by the user is used to train the AI model and add the new created few-shot prompt to the repositories. When the user begins inputting the query, the application interface provides for user's selection one or more few-shot prompts for generating output results in a preferred format. The user may select one or more few-shot prompts from the application interface. Further, the user interface also provides a portion which depicts few-shot prompts for selection by the user. The user, based on his preference, may select one or more prompts which is inputted as a pre-condition for generating the output results. In an embodiment, the user may deny using any few-shot prompt and the system may provide the search results according to a predetermined or default format.

In Step 904, a query from the user is received on the application interface. The query generation module receives the user's query which may be related to one or more products saved in the database. Further, the user's query through the application interface may be based on index prompt and few-shot prompt. The index prompt module is configured to provide the customer one or more index-based searching capabilities. Further, the few shot prompt module is configured to provide one or more few shot prompts to the customer for selection, based on preferred format of the output. The user's query generated according to the indexing and the few shot prompt is forwarded to the database for retrieving the relevant results based on semantic vector similarity between the query and information stored in the database.

In Step 905, the user's query may be a simple text-based query which is processed by the natural language processing technique to identify the key terms and relationships between one or more words included in the search query. an Artificial Intelligence Model (AI) is provided which is configured to process the customer's query to generate vector index and vector embeddings.

In Step 906, the user's query is forwarded to the database by the query module.

In Step 907, one or more search results are retrieved based on semantic similarity or vector similarity between the user's query and data stored in the vector database. In an embodiment, the vector embeddings of the search query are compared with the vector embeddings of the data stored in the database and based on similarly score, relevant data is retrieved. In an example, a similarity score may be assigned and the data is retrieved based on matching vector embeddings if the similarity score is above a threshold level. The system is further configured to change the threshold on the similar score if the retrieved results are not matching the quality score.

In Step 908, the search results are displayed on the application interface. In displaying the search results, the application interface provides a portion which displays one or more output relating to search query is provided according to the user's selection of few-shot prompts and indexes. In an exemplary embodiment, the user may select one or many outputs based on selection icon and generate a report using the "download" icon. Also, the query results are saved in the memory using the "save" icon.

FIG. 10 illustrates the method steps for generating indexes based on data stored in the vector database, in accordance with an embodiment of the present invention.

In Step 1001, one or more entities data are stored in the database. An entity which manufactures products such as healthcare products, devices/medicines issue annual reports and such annual reports including other information pertaining to such medicines/devices/healthcare products are generally accessible by the customer/end users through different sources such as company website or other common portals which aggregate multiple reports of one or more companies. The information pertaining to products may include its performance statistics, trial results, details of clinical trials, efficacy information etc. A common end user who wish to view such report generally is able to download such reports and make conclusions based on such reports.

In Step 1002, the database is configured to save the data related to one or more products pertaining to plurality of entities based on vector indexes and embeddings. An embedding is a representation of words, sentences, images summarized as an array of numericals, i.e., vectors and these embeddings captures semantic information about one or more terms or phrase. In an embodiment, the database processes the data by establishing relationship between two or more products and create indexes based on relationship. Further, semantic similarity or relatedness of products are established using natural language processing and one or more relationships between various products, entities are created based on similarity scores.

In Step 1003, one or more vector embeddings and indexes stored in the database is accessed. The vector database is configured to save the data related to one or more products pertaining to plurality of entities based on vector indexes and embeddings. The vector database processes the data by establishing relationship between two or more products and create indexes based on relationship. Further, semantic similarity or relatedness of products are established using natural language processing and one or more relationships between various products, entities are created based on similarity scores. The Index prompt module of the query module access the vector database to retrieve the vector embeddings and indexes.

In Step 1004, the Index prompt module applies filters to the accessed vector embeddings. For example, one or more filters are applied to the retrieved embeddings from the vector store. By applying filters, one or more indexes are created by the index prompt module.

In Step 1005, the index prompt module creates indexing strategies based on accessing the vector store. In generating the indexes, the index Prompt Module is coupled to AI model and is configured to access the indexing stored in the vector database and accordingly, creates one or more indexing strategies for the user's selection. In one embodiment, the index prompt module applies filters while retrieving embeddings from a vector store and use the similarity search method to retrieve embeddings based on a query. The indexing generated by Index prompt module may include hierarchical indexing which includes product indexes, Department indexes, Chapter Indexes. Based on entities data stored in the database and its vector indexing, the index prompt module is configured to generate a different type of indexing such as hierarchical indexing, flat indexing.

In Step 1006, the index prompt module is configured to provide one or more index strategies to the user for selection while inputting the search query. After generating indexes based on vector database, the index prompt module is further configured to provides prompt to the user for selection of one or more index strategy when the user is inputting a search query. The user may refrain from selecting an indexing strategy and continue to input the search without any indexing criteria. The user interface provides a portion which depicts indexes to be selected by the user. In an exemplary embodiment, the user may utilize "Select" icon to select one or more indexes from the plurality of indexes provided on the user interface. In another embodiment, the user may deny using any indexes for the purpose of initiating the search based on the inputted query.

The system and method proposed in the present disclosure may thereby be used for generating accurate search results based on indexes and few-shot prompts. A user who is desirous of accessing information from the database (like healthcare related products, their reports on efficiency/performance) can run a search query and execution of such query may return results to the end user. The present disclosure results in efficiency of retrieving relevant search results by using indexes created based on database vector database and adding few-shot prompts for use by the user. With the provided solution, the user may select indexes generated by the system and also, customize the output results by using few-shot prompts, thereby retrieving the relevant search results with more accuracy and in desired format, thereby making query generation process and results retrievable more relevant and useful.

The system provides a machine learning model which steers the query generation process by learning about the patterns and selection by one or more user based on their access. few-shot prompting is used as a technique to enable in-context learning where the demonstrations may be provided in the prompt to steer the model to better performance.

In some embodiments, the network may be a public network (e.g., the Internet), a private network (e.g., an internal localized, or closed-off network between particular devices). In some other embodiments, the network may be a hybrid network (e.g., a network enabling internal communications between particular connected devices and external communications with other devices). In various embodiments, the network may include one or more relay(s), router(s), switch(es), routing station(s), and/or the like.

The figures of the disclosure are provided to illustrate some examples of the invention described. The figures are not to limit the scope of the depicted embodiments or the appended claims. Aspects of the disclosure are described herein with reference to the invention to example embodiments for illustration. It should be understood that specific details, relationships, and method are set forth to provide a full understanding of the example embodiments. One of ordinary skill in the art recognize the example embodiments can be practiced without one or more specific details and/or with other methods.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Aspects of the present disclosure may be implemented as computer program products that comprise articles of manufacture. Such computer program products may include one or more software components including, for example, applications, software objects, methods, data structure, and/or the like. In some embodiments, a software component may be stored on one or more non-transitory computer-readable media, which computer program product may comprise the computer-readable media with software component, comprising computer executable instructions, included thereon. The various control and operational systems described herein may incorporate one or more of such computer program products and/or software components for causing the various conveyors and components thereof to operate in accordance with the functionalities described herein.

A software component may be coded in any of a variety of programming languages. An illustrative programming language may be a lower-level programming language such as an assembly language associated with a particular hardware architecture and/or operating system platform/system. Other example of programming languages included, but are not limited to, a macro language, a shell or command language, a job control language, a script language, a database query, or search language, and/or report writing language. In one or more example embodiments, a software component comprising instructions in one of the foregoing examples of programming languages may be executed directly by an operating system or other software component without having to be first transformed into another form. A software component may be stored as a file or other data storage methods. Software components of a similar type or functionally related may be stored together such as, for example, in a particular directory, folder, or repository. Software components may be static (e.g., pre-established, or fixed) or dynamic (e.g., created or modified at the time of execution).

While this specification contains many specific implementation details, these should not be construed as limitations on the scope of any disclosures or of what may be claimed, but rather as descriptions of features specific to particular embodiments of particular disclosures. Certain features that are described herein in the context of separate embodiments can also be implemented in combination in a single embodiment. Conversely, various features that are described in the context of a single embodiment can also be implemented in multiple embodiments separately or in any suitable sub combination. Moreover, although features may be described above as acting in certain combinations and even initially claimed as such, one or more features from a claimed combination can in some cases be excised from the combination, and the claimed combination may be directed to a sub combination or variation of a sub combination.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

It is to be understood that the disclosure is not to be limited to the specific embodiments disclosed, and that modifications and other embodiments are intended to be included within the scope of the appended claims. Although specific terms are employed herein, they are used in a generic and descriptive sense only and not for purposes of limitation, unless described otherwise.

We claim:

1. A system for providing virtual assistant for generating a customized query for retrieving data from a database, comprising:

a processor, a memory storing program instructions which, when executed by the processor, causes the processor to:

create one or more index of categories of data specific to one or more user;

provide the one or more index of categories of the data, for efficient retrieval of the data from the database based on a user's query;

provide one or more few-shot prompts for use by the user for generating an output in a predetermined format corresponding to the query;

receive a query from the one or more user, wherein said query is a text and is based on at least one of index of categories and the few-shot prompt;

process the query using natural language processing to extract one or more textual content from the query;

send the query to the database for retrieval of the data;

retrieve the relevant data based on identified textual content, said relevant data is based on semantic similarity between the vector index; and display the retrieved data to the one or more user based on the predetermined format specified by few-shot prompt.

2. The system of claim 1, wherein the processor is further configured to:

create one or more few-shot prompt specific to one or more user.

3. The system of claim 1, wherein the processor is further configured to:

train an AI model based on selection of index of categories of the data and few-shot prompt by one or more user.

4. The system of claim 1, wherein the one or more index of categories of data includes hierarchical indexing or flat indexing.

5. The system of claim 4, wherein the hierarchical indexing comprises tenant, product, department, and chapter indexes, and the flat indexing links categories directly to the entity.

6. The system of claim 1, wherein, in retrieving the data, the processor is configured to:

access the database which stores the one or more data with vector embeddings.

7. The system of claim 1, wherein the processor is further configured to:

automatically update the index of categories of the data based on change in vector index of the data stored in the database.

8. The system of claim 1, wherein the processor is further configured to receive a user-defined few-shot prompt and store the prompt in a repository for subsequent use.

9. A method for providing a virtual assistant for generating a customized query for retrieving data from a database, comprising:

creating one or more index of categories of data specific to one or more user;

providing the one or more few-shot prompts for use by the user for generating an output in a predetermined format corresponding to the user's query;

receiving a query from the one or more user, wherein said query is a text and is based on at least one of index of categories and the few-shot prompt;

processing the query using natural language processing to extract one or more textual content from the query;

sending the query to the database for retrieval of the data;

retrieving the relevant data based on identified textual content, said relevant data is based on semantic similarity between the vector index; and displaying the retrieved data to the one or more user based on the predetermined format specified by few-shot prompt.

10. The method of claim 9, further comprising:

creating one or more few-shot prompt specific to one or more user.

11. The method of claim 9, further comprising:

training an AI model based on selection of index of categories of the data and few-shot prompt by one or more user.

12. The method of claim 9, wherein the one or more index of categories of data includes hierarchical indexing or flat indexing.

13. The method of claim 9, comprising:

accessing the database which stores the one or more data with vector embeddings.

14. The method of claim 9, comprising:

updating the index of categories of the data based on change in vector index of the data stored in the database.

15. A non-transitory computer-readable storage medium storing program instructions providing a virtual assistant for generating a customized query for retrieving data from a database, the instructions, when executed, perform the steps of:

creating one or more index of categories of data specific to one or more user;

providing the one or more index of categories of the data, for efficient retrieval of the data from the database based on a user's query;

providing one or more few-shot prompts for use by the user for generating an output in a predetermined format corresponding to the user's query;

receiving a query from the one or more user, wherein said query is a text and is based on at least one of index of categories and the few-shot prompt;

processing the query using natural language processing to extract one or more textual content from the query;

sending the query to the database for retrieval of the data;

retrieving the relevant data based on identified textual content, said relevant data is based on semantic similarity between the vector index; and displaying the retrieved data to the one or more user based on the predetermined format specified by few-shot prompt.

16. The non-transitory computer-readable storage medium as claimed in claim 15, further comprising program instructions to perform the steps of:

creating one or more few-shot prompt specific to one or more user.

17. The non-transitory computer-readable storage medium as claimed in claim 15, further comprising program instructions to perform the steps of:

training an AI model based on selection of index of categories of the data and few-shot prompt by one or more user.

18. The non-transitory computer-readable storage medium as claimed in claim 15, further comprising program instructions to perform the steps of:

accessing the database which stores the one or more data with vector embeddings.

19. The non-transitory computer-readable storage medium as claimed in claim 15, further comprising program instructions to perform the steps of:

updating the index of categories of the data based on change in vector index of the data stored in the database.

\* \* \* \* \*